(12) United States Patent
Wei

(10) Patent No.: US 6,919,348 B2
(45) Date of Patent: *Jul. 19, 2005

(54) THERAPEUTIC 1,2,3,6-TETRAHYDROPYRIMIDINE-2-ONE COMPOSITIONS AND METHODS THEREWITH

(76) Inventor: Edward T. Wei, 480 Grizzly Peak Blvd., Berkeley, CA (US) 94708

(*) Notice: Subject to any disclaimer, the term of this patent is extended or adjusted under 35 U.S.C. 154(b) by 168 days.

This patent is subject to a terminal disclaimer.

(21) Appl. No.: 10/139,193

(22) Filed: May 2, 2002

(65) Prior Publication Data

US 2003/0207851 A1 Nov. 6, 2003

(51) Int. Cl.[7] .................. A61K 31/513; A61K 38/18
(52) U.S. Cl. .................. 514/269; 514/345; 514/318; 544/318
(58) Field of Search ............... 514/269, 345, 514/318, 343; 544/318

(56) References Cited

U.S. PATENT DOCUMENTS

| | | | |
|---|---|---|---|
| 3,821,221 A | 6/1974 | Podesva et al. | 260/251 |
| 5,116,868 A | 5/1992 | Chen et al. | 514/546 |
| 5,800,485 A | 9/1998 | Trop et al. | 607/105 |
| 6,166,044 A | 12/2000 | Sandborn et al. | 514/343 |
| 6,365,190 B1 | 4/2002 | Gordon et al. | 424/489 |

OTHER PUBLICATIONS

John S. James, AIDS Treatment News No. 074 –Feb. 10, 1989.*
Merck Index, Twelfth Edition, p. 551, (No. 3309), Editor Susan Budavari, (1996).*
Tse, S.Y.H. and Wei, E.T. (AN 1987:12803, Caplus–STN, Psychopharmacology *Berlin, Germany) (1986), 90(3), p–322–6).*
Babes, et al, Cooling inhibits capsaicin . . . Neuroscience Letters 317: 131–134; 2002.
Barnes P.J. Neurogenic inflammation in the airways. Respiratory Physiology 125: 145–154, 2001.
Handwerker, et al., Discharge patterns of human C–fibers induced by itching and burning stimuli. J. Neurophysiol. 66: 307–315, 1991.
McKemy et al, Identification of a cold receptor reveals a general role for TRP channels in thermosensation. Nature 416: 52–58, 2002.
Nair, B., Final report on the safety assessment of Mentha Piperita (Peppermint) Oil, . . . Int. J. Toxicol. 20 Suppl 3: 61–73, 2001.
Watson, H. R., R. Hems, D.G. Roswell & D. J. Spring, New compounds with the menthol cooling effect, J. Society Cosmetic Chemists. 29, 185–200 (1978).
Wei, E.T. Chemical stimulants of shaking behavior. Journal Pharmacy and Pharmacology 28: 722–724, 1976.
Wei, E.T. Pharmacological aspects of shaking behavior produced by AG–3–5, TRH, and morphine withdrawal. Federation Proceedings 40: 1491–1496, 1981.
Wei, E.T. and D.A. Seid. AG–3–5: A chemical producing sensations of cold. Journal Pharmacy and Pharmacology 35: 110–112, 1983.

* cited by examiner

*Primary Examiner*—Sabiha N. Qazi

(57) ABSTRACT

A therapeutic composition is provided that comprises a 1-R1-phenyl, 4-R2-phenyl substituted 1,2,3,6-tetrahydropyrimidine-2-one cold receptor agonist in a therapeutically effective amount and preferably further comprises one or more pharmaceutically active drugs such as an anti-inflammatory glucocorticosteroid, a sympathomimetic amine decongestant, an anti-histamine, a local anesthetic, menthol or a menthol analog, and mixtures thereof. The cold receptor agonist may be represented by the general formula 1-[R1-phenyl]-4-[R2-phenyl]-1,2,3,6-tetrahydropyrimidine-2-one wherein: R1 is -hydroxy, -chloro, -fluoro, -alkyl, -acetoxy, -trifluoromethyl; and R2 is -nitro, -chloro, -fluoro, -alkyl, -trifluoromethyl. Therapeutic compositions of the invention elicit long-lasting cooling or soothing, particularly when formulated for delivery to suppress the sensations of itch and pain, such as for delivery to inflamed skin, to the mucous membranes of the anogenital areas, and to the enteric mucosa.

5 Claims, No Drawings

THERAPEUTIC 1,2,3,6-TETRAHYDROPYRIMIDINE-2-ONE COMPOSITIONS AND METHODS THEREWITH

CROSS-REFERENCE TO RELATED APPLICATIONS

Not applicable.

STATEMENT REGARDING FEDERALLY SPONSORED RESEARCH OR DEVELOPMENT

Not applicable.

BACKGROUND OF THE INVENTION

1. Field of the Invention

This invention generally relates to a class of chemicals that specifically activate the cold receptors and therapeutic use of these chemicals. This invention more particularly relates to therapeutic compositions eliciting long-lasting cooling or soothing properties, particularly when formulated for delivery to suppress the sensations of itch and pain, such as for delivery to inflamed skin, to the mucous membranes of the anogenital areas, and to the enteric mucosa. The particularly preferred embodiment compositions comprise "icilin", a 1,2,3,6-tetrahydropyrimidine-2-one compound.

2. Description of Related Art

Human awareness of the external environment is conveyed by specialized organs for sight, smell, sound, taste, touch and pressure. In addition to these sensory modalities, there are present in the skin, mucous membranes, and gut, specialized nerve endings for detecting heat, cold, pain and itch.

Sensory mechanisms and inflammation. Small-diameter nerve fibers, mostly unmyelinated, carry the afferent nerve signals that are decoded in the brain as sensations of heat, cold, pain and itch. On the nerve fibers are specialized receptors that respond to temperature changes and to chemicals that produce sensations of heat and cold, such as capsaicin the active ingredient of chili peppers and menthol the active ingredient of mentha leaves. The intense stimulation of heat and pain fibers can cause the concurrent release of neuroactive peptides such as substance P from the sensory nerves and this release exacerbates tissue injury, a phenomenon known as "neurogenic inflammation."

Anti-inflammatory effects of cold-receptor activation. The ability of ice applied to the skin or to the orbit to suppress the pain of burns or other forms of traumatic injury is well known. An ice cube in the mouth will also suppress a toothache. The precise mechanisms of pain relief by cold are not clear but it has been shown in animal experiments that the discharge of pain fiber afferents are decreased by contact with surfaces of solids with a low temperature such as ice. Menthol, a chemical that activates the cold receptor, does not suppress severe pain, but the cooling sensations that it evokes on the skin and mucous membranes are refreshing and counteracts heat and irritation. Thus, menthol is used as a component in a wide range of toiletries, liniments and lotions for topical application on the skin, and as a flavoring and refreshing agent in foodstuffs, beverages, toothpastes, skin rubs, and mouthwashes. Menthol is also used as a tobacco additive for producing a cool sensation in the mouth and upper respiratory tract when smoking.

Background on icilin. 1,2,3,6-Tetrahydropyrimidine-2-one compounds were described in U.S. Pat. No. 3,821,221 (inventors C. Podesva and J. M. Do Nascimento., Jun. 28, 1974). These compounds were thought to have depressant and/or stimulant effects on the central nervous system. In 1972, an abstract described a compound in this series called AG-3-5 (1[2-hydroxyphenyl]-4-[3-nitrophenyl]-1,2,3,6-tetrahydropyrimidine-2-one). This prototype elicited a syndrome of "wet dog shake behavior" in rats and monkeys accompanied by hyperthermia, hyperactivity and ptosis. Wei (Chemical stimulants of shaking behavior. Journal of Pharmacy and Pharmacology 28: 722–724, 1976) provided the first detailed report of the actions of AG-3-5 in animals and noted that shaking behavior similar to those of a dog when wet could be evoked in various laboratory animals such as the rat, mouse, cat, dog, gerbils, guinea pigs and hamsters. Subsequently, Wei (Pharmacological aspects of shaking behavior produced by AG-3-5, TRH, and morphine withdrawal. Federation Proceedings 40: 1491–1496, 1981) reported that 0.1 mg of AG-3-5 applied to the dorsum of the tongue elicited prickling sensations of cold and ingestion of 6 mg, on one occasion out of three, produced sensations of coolness on the cheeks and on the inner surfaces of the arms and legs. It was hypothesized that AG-3-5 may produce specific activation of receptors for cold, and that stimulation of these receptors accounted for the shaking seen in laboratory animals. In a subsequent publication E. T. Wei and D. A. Seid. AG-3-5: A chemical producing sensations of cold Journal of Pharmacy and Pharmacology 35: 110–112, 1983) the effects of AG-3-5 on shaking behavior in the rat were compared to those of menthol and AG-3-5 was shown to be 400 times more potent than menthol on a molar basis on this behavioral endpoint. AG-3-5 was less toxic than menthol, as measured by the oral median lethal dose in rats. AG-3-5 was named icilin because of its cold-producing properties.

Recently, two independent groups simultaneously cloned a biological macromolecule (called receptor) from trigeminal sensory neurons of the rat. These receptors belong to the transient receptor potential (TRP) family of ion channels and responded to cold temperature and to menthol. Using a sample provided by Wei, McKemy et al. (Identification of a cold receptor reveals a general role for TRP channels in thermosensation. Nature 416: 52–58, 2002) showed that icilin was about 200 times more potent than menthol in eliciting ion channel current changes in the cloned and transfected TRP(M8) receptor. The ion permeability changes elicited in transfected cells were more robust with icilin than those elicited by menthol, and the presence of extracellular calcium was required for activity. Menthol currents did not require extracellular calcium.

The chemical structure of icilin bears little similarity to that of menthol; the former one being a pyrmidine-2-one attached to two phenyl rings, and the latter a cyclohexanol derivative. Activation of the TRP(M8) receptor on the neuronal membrane may lead to depolarization of the sensory nerve ending and send action potentials towards the spinal cord and brain that are eventually recognized as psychic signals of cold.

Most of the known cooling agents used in commerce as consumer products to reduce irritation in the skin and mucous membranes have chemical structures similar to menthol and are based on a cyclohexanol template. For example, Vicks Corporation, a division of Proctor and Gamble, sells a variety of products for upper respiratory ailments, including the common cold, cough and bronchitis. The active ingredient(s) in VapoSteam® is camphor (a cough suppressant with chemical structure similar to menthol) and in VapoRub® menthol and camphor. Other ingredients used are: Vapor Inhaler® (levamphetamine, as a nasal decongestant), NyQuill Cough® (dextromethorphan, an antitussive and an antihistamine). Vicks 44® anticough syrup also contains dextromethorphan as the primary antitussive.

Although drugs such as camphor, menthol, phenol, salicylic acid, tar, capsaicin, and petrolatum are part of dermatological preparations to reduce skin irritation, they have limited anti-pruritic effect and are often of short duration. Devices to physically lower tissue temperature with ice probes have also been used for anorectal discomfort (U.S. Pat. No. 5,800,485).

A need exists for therapeutic compositions useful on inflamed skin and the mucous membranes of the anogenital areas for itching and for the discomforts of hemorrhoids.

BRIEF SUMMARY OF THE INVENTION

In one aspect of the present invention, a therapeutic composition is provided that comprises a 1-R1-phenyl, 4-R2-phenyl substituted 1,2,3,6-tetrahydropyrimidine-2-one cold receptor agonist in a therapeutically effective amount and preferably further comprises one or more pharmaceutically active drugs such as an anti-inflammatory glucocorticosteroid, a sympathomimetic amine vasocontrictor or decongestant, an anti-histamine, a local anesthetic, menthol or a menthol analog, and a carminative. The cold receptor agonist may be represented by the general formula 1-[R1-phenyl]-4-[R2-phenyl]-1,2,3,6-tetrahydropyrimidine-2-one wherein: R1 is -hydroxy, -chloro, -fluoro, -alkyl (with about 2 to 4 carbons), -acetoxy, -trifluoromethyl ; and R2 is -nitro, -chloro, -fluoro, -alkyl, -trifluoromethyl.

A particularly preferred cold receptor agonist embodiment is called "icilin" and a particularly preferred composition has icilin dispersed as an emulsion in a dermatologically acceptable vehicle. Thus, icilin formulated and administered as a liniment, and preferably in combination with one or more pharmaceutically active drugs, offers improved therapeutic benefit for the treatment of pruritus.

Icilin has a relatively long duration of activity in the body and, in contrast to menthol, the actions of the less soluble icilin are modulated by the mode of drug delivery.

In another aspect of the invention, icilin or an icilin analog is formulated for localized delivery to the colon in the treatment of irritable bowel.

Other advantages and aspects of the present invention will be understood by reading the following detailed description and the accompanying claims.

DETAILED DESCRIPTION OF THE INVENTION

Compositions and therapeutic methods in accordance with this invention utilize a 1-R1-phenyl, 4-R2-phenyl substituted 1,2,3,6-tetrahydropyrimidine-2-one cold receptor agonist, preferably of the general formula 1-[R1-phenyl]-4-[R2-phenyl]-1,2,3,6-tetrahydropyrimidine-2-one wherein: R1 preferably is -hydroxy, -chloro, -fluoro, -alkyl (with about 2 to about 4 carbon atoms) -acetoxy, -trifluoromethyl; and R2 preferably is -nitro, -chloro, -fluoro, -alkyl (with about 2 to 4 carbons), -trifluoromethyl. I refer to the particularly preferred compound and its analogs as "icilin" and its analogs as "icilin analogs". Formula 1 illustrates the general formula and icilin is represented by Formula 2.

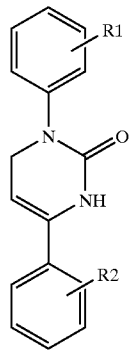

Formula 1: 1-R1-phenyl, 4-R2-phenyl, substituted 1,2,3,6-tetrahydropyrimidine-2-one.

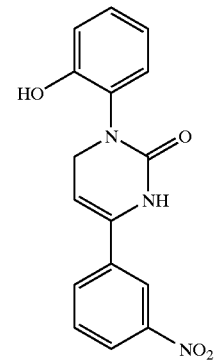

Formula 2: Icilin, 1-[2-hydroxy]-4-[3-nitrophenyl]-1,2,3,6-tetrahydropyridimine-2-one.

Icilin is a lemon yellow crystalline powder with a molecular weight of 311 Daltons and a melting point of 229 to 231° C. The powder is without odor and non-irritating, meaning that it does not elicit any smell or unpleasant sensations upon contact with the surfaces of the human body. The compound is stable at room temperature. Icilin is readily soluble in organic solvents such as dimethylsulfoxide, nitromethane, dimethylacetamide and propanediols; slightly soluble in ethanol and acetone; and virtually insoluble in water. Thus, icilin would be considered as a lipophilic, hydrophobic compound that is not easily miscible with aqueous systems. Analogs of icilin, for example, with acetyoxy, ethyl, fluoro, or trifluoromethyl substitutions, retain similar chemical and physical properties and are included within the scope of this invention.

Methods suitable for the preparation of the Formula 1 and Formula 2 compounds are described by Podesva and Do Nascimento, U.S. Pat. No. 3,821,221, issued Jun. 28, 1974, incorporated herein by reference, and are exemplified by Example A hereinafter.

Menthol, by contrast, is a white crystal with a molecular weight of 156 Daltons and a melting point of 41 to 43° C., a temperature slightly above body temperature. Menthol has a characteristic peppermint odor and in high concentrations is irritating to the eyes and elicits taste sensations on the tongue and oropharynx. Menthol is more hydrophilic than icilin being soluble in ethanol and slightly soluble in water. Some analogs of menthol, e.g. (+)-neomenthol are colorless liquids at room temperature.

The physico-chemical differences between icilin and menthol confer unique advantages to icilin for manipulating sensory nerve discharges in certain defined clinical situations, as described hereinafter. The first advantage is the site of delivery: menthol cannot be delivered to the eyelids and its environs, the nasal membranes, or the mucous membranes of the anogenital region at high concentrations because it is pungent, stings and irritates. Icilin, on the other hand, can be administered to these sites because it is non-irritating. A second major advantage of icilin is its duration of action. Icilin's actions can be localized at its site of application for a prolonged period because of its lipophilic characteristics and because it can be administered as a powder or dispersed (either in solid form or solubilized) as an emulsion. By contrast, menthol is volatile and rapidly re-distributes and metabolizes in the body so its duration of action is relatively short. For example, icilin applied to nasal membranes can produce refreshing sensations for up to 3 hours. By contrast, menthol applied to the skin or mucous membranes generally does not produce cooling sensations for longer than 15 to 30 minutes, regardless of dose.

As described herein, icilin is shown to be useful as an active antipruritic agent in the anogenital region. Also, icilin, formulated as an eye-drop, relieves eye irritation. Yet further, icilin may be encapsulated and administered to relieve irritation in the gut mucosa. One major conclusion is in practicing this invention that icilin, applied to inflamed skin and mucous membranes, will relieve itch.

Icilin is particularly contemplated for use when it is combined (used as an adjuvant) with other drugs such as anti-inflammatory glucocorticosteroids, sympathomimetic amine decongestants, anti-histamines, local anesthetics, menthol and menthol analogs, or a carminative such as peppermint oil. Icilin administered in combination with such drugs offers greater therapeutic benefit than formulations that do not include icilin.

General Formulation of Icilin Compounds for Delivery to the Cold Receptor

The formulations of icilin for delivery to cold receptors depend on the accessibility in various tissue beds and the desired duration of action. Standard ointment and lotion formulations may be used for delivery to inflamed skin and to the mucous membranes of the anogenital areas. Thus, particularly preferred embodiments of this invention are wherein icilin is used as an adjuvant so as to improve the efficacy of the ointment or lotion because it reduces the patient's sense of discomfort and itch and alleviates some aspects of the inflammation.

The surprisingly long duration of action of icilin greatly expands the efficacy of treatment. Particularly preferred lotion or ointment compositions with icilin as adjuvant and useful for delivery to inflamed skin and to the mucous membranes of the anogenital areas include one or more of an anti-inflammatory analgesic agent, an anti-inflammatory steroidal agent, or a sympathomimetic amine decongestant/vasoconstrictor (such as phenylephrine hydrochloride and oxymetazoline). Suitable such agents are more fully described hereinafter.

For delivery to cold receptors lining the nasal cavity, icilin dissolved first in an inert solvent such as propanediol and then suspended in aqueous saline, can be delivered with a nebulizer. In such a device, commonly used for delivering a decongestant in a nasal spray, liquid droplets, of a size pattern not likely to penetrate the lower respiratory tract, are generated by manual pressure on a squeeze bottle with a defined nozzle size. The drug effects are then localized to the nasal cavity.

For delivery to the cold receptors located in the mucous membranes of the upper airways (bronchi and bronchioles), icilin may be delivered is soluble form with standard metered dose inhalers or as a crystalline material in dry powder inhalers. Both methods of delivery allow precise control of dosage and location of drug delivery.

For delivery to cold receptors in the skin or mucous membranes, the physical features of the icilin molecule may be modified to confer greater accessibility to the target. For example, the drug may be re-crystallized or micronized to a smaller particle diameter and/or greater surface area to facilitate solubility in tissues. A standard skin permeability enhancers such as surfactants may be used for increasing penetration to receptors in the skin, and a standard drug carrier such as petrolatum or liposomes may be used for drug delivery.

Yet further, icilin may be applied as a liniment or encapsulated in and/or bound to resins with chemical bonds that are selectively cleaved in the intestinal tract to access cold receptors in enteric tissues. Further description of such embodiments is given below.

Treatment of Pruritus

The skin is composed of three layers: the epidermis, the dermis and the subcutaneous fatty tissue. The epidermis varies in thickness from 0.15 to 0.80 mm and its outermost part, called the stratum corneum (horny layer), is built of several layers of flattened, dehydrated, keratinised cells. The dermis is 3 to 5 mm thick and it contains collagen fibers, blood and lymphatic vessels, hair follicles, sebaceous and sweat glands and the drug target—the sensory nerve endings.

The ability of ice, applied to inflamed or injured tissues, to numb the senses, to suppress pain and itch, is a fact of human experience. The ability of ice to elicit reflex vasoconstriction and to lower local tissue temperatures is, of itself, inadequate to explain the absence of pain because vasoconstrictive agents are not analgesic and the lowering of temperature is superficial. One cogent explanation for the pain-killing properties of ice is that the elicited increase in discharge of cold sensory afferents suppresses the afferent signal from nociceptor and other afferents.

It has been shown that menthol will elevate the threshold temperature for nociceptor afferent discharge, but menthol has limited analgesic activity. Some commercial over-the-counter analgesic and anti-itch preparations contain menthol as the active ingredient. For example, extra strength Icy Hot® Patch contains 5% menthol in an occlusive bandage. Anti-Itch Medicated Cream from Walgreens contains 1% menthol and 1% pramoxine hydrochloride, a local anesthetic.

Itch is a familiar sensory state associated with the desire to scratch. Itching and scratching are phenomena common to humans and animals. The sensory nerves that initiate itch have not been precisely identified but are thought to be unmyelinated C-fibers, with nerve endings located between the epidermis and dermis. In medical terminology, severe itching is called pruritus and drugs that suppress itching are anti-pruritic agents. Many inflammatory and irritating conditions of the body are expressed as itching together with pain. Itching occurs mainly on skin, on mucous membranes, and on the conjunctiva. One aspect of this invention is to relieve itch with an anti-pruritic composition.

Pruritus of the skin may be caused by dermatoses such as contact dermatitis, atopic dermatitis, psoriasis, seborrheic dermatitis, autosensitization dermatitis, asteatosis, senile pruritus, photosensitive dermatosis, urticaria, prurigo, impetigo, eczema, lichen, sunburn, and acne vulgaris. Included in such dermatoses is also itching caused by poison oak, and allergies to plants such as oak and sumac.

Neurophysiological studies show that pain and itch sensations are transmitted by an identical detection and cable transmission system. The discharge patterns of human C-fibers induced by itching and burning stimuli have been studied by the use of microneurography of unmyelinated afferents in healthy volunteers. Histamine applied to the receptive fields of these units provoke itching sensations and a solution containing 20 or 30% mustard oil applied to the receptive field of the respective unit provoked a sensation of burning pain. Analysis of the spike discharge patterns showed no evidence for a separate encoding of itch and burning pain in the C-fiber unit. (Handwerker, H. O.; Forster, C.; Kirchhoff, C., Discharge patterns of human C-fibers induced by itching and burning stimuli. J. Neurophysiol. 66: 307–315; 1991.) Hence, inhibition of one sensory modality with a drug such as icilin is likely to have an identical attenuation of the other.

Pruritus of the skin may also be caused by infectious agents such as herpes virus (for example, itchy cold sores from herpes simplex virus), insects and parasites. For example, scabies is caused by a tiny mite (*Sarcoptes scabiei*). The mites burrow into the skin and cause itching. The mites may be removed by drugs such as permethrin but the residual mite fragments can initiate an allergic state leading to severe itching. Pediculosis is an infestation of the hairy parts of the body or clothing with the eggs, larvae or adults of lice. The crawling stages of this insect feed on human blood, which can result in severe itching. Head lice are usually located on the scalp, crab lice in the pubic area and body lice along seams of clothing. Problems with lice infestations afflict million of Americans, particularly school children. Enterobiasis (pinworm) is caused by a small, white intestinal worm called *Enterobius vermicularis*. Pinworms are about the length of a staple and live in the rectum of humans. While an infected person sleeps, female pinworms leave the intestines through the anus and deposit eggs on the surrounding skin. Itching around the anus, disturbed sleep, and irritability are common symptoms. Fungal infections of the skin, for example, athlete's foot, and infections of the anogenital region, for example, yeast infections in women, are also conditions that cause pruritus.

Conjunctivitis ("pink eye") is caused by inflammation of the membranes of the ocular orbit and may lead to severe itching. Examples of visceral diseases complicated with pruritus and being particular problems include malignant tumors, diabetes mellitus, hepatic diseases (especially cholestasis), renal failure, hemodialysis, and pregnancy.

The anorectal region is a frequent location for inflammation and itch. Hemorrhoids are a principal cause of itch, as well as soiling of the skin from diarrhea, such as may occur in irritable bowel disease. Enterobiasis, as described above, is another cause of itching in this region.

Current drug therapies for the treatment of itch include orally administered drugs such as glucocorticosteroids, sedative antihistamines, and some tricyclic compounds, such as doxepin hydrochloride, but these lack efficacy or, upon continued use, have undesirable side effects. Topical anti-inflammatory glucocorticoids are widely used for dermatoses and have short-term effectiveness for reducing inflammation. Prolonged use, however, results in thinning of the skin and the possibility of super-infection.

The significance of itching in clinical conditions is illustrated by the condition known as atopic dermatitis. Atopic dermatitis is a chronic inflammatory skin disorder exhibited by individuals with a hereditary predisposition to a lowered cutaneous threshold to pruritis, often accompanied by allergic rhinitis, hay fever, and asthma. The condition is characterized by extreme itching, leading to scratching and rubbing that in turn results in the typical lesions of eczema.

In infants (infantile eczema), there is a predilection for occurrence of itch on the cheeks, which may extend to other areas of the body. In older children, adolescents and adults, it is found chiefly on the flexural surfaces, especially on the antecubital (elbow) and popliteal (knee) areas, and on the neck, eyelids, and wrists and behind the ears.

Affected children will scratch even when asleep for up to 2 out of 8 hours of sleep (versus a few minutes for normal children) and the excoriations can lead to bleeding and infection. Atopic dermatitis and eczema, if sufficiently severe, can lead to death. Less serious, but uncomfortable and often painful symptoms associated with atopic dermatitis include swelling, redness, blisters, crusting, ulceration, pain, scaling, skin cracking, hair loss, scarring, or oozing of fluid involving the skin, eye, or mucous membranes. Under current therapy, topical glucocorticosteroids are only partially effective in treating this condition.

Compositions of the present invention with icilin and/or icilin analogs are preferably formulated as linimens with a dermatologically acceptable vehicle in which icilin and/or icilin analogs are dispersed, and may preferably further comprise a single pharmaceutical or a combination of pharmaceuticals. Pharmaceuticals that may be used, either alone or in combination, include anti-inflammatory analgesic agents, anti-inflammatory steroidal agents, antihistamines, sympathomimetic amine vasoconstrictors, menthol and menthol analogs, local anesthetics, antibiotics and keratolytics.

Examples of anti-inflammatory analgesic agents include methyl salicylate, monoglycol salicylate, aspirin, indomethacin, diclofenac, ibuprofen, ketoprofen, naproxen, pranoprofen, fenoprofen, sulindac, fenclofenac, clidanac, flurbiprofen, fentiazac, bufexamac, piroxicam, pentazocine, etc.

Examples of steroidal anti-inflammatory agents include hydrocortisone, prednisolone, dexamethasone, triamcinolone acetonide, fluocinolone acetonide, hydrocortisone acetate, prednisolone acetate, methylprednisolone, dexamethasone acetate, betamethasone, betamethasone valerate, flumetasone, fluticasone, fluorometholone, beclomethasone diprorionate, etc.

Examples of antihistamines include diphenhydramine hydrochloride, diphenhydramine salicylate, diphenhydramine, chlorpheniramine maleate, promethazine hydrochloride, etc.

Examples of sympathomimetic amine vasoconstrictors include phenylephrine hydrochloride and oxymetazoline.

Examples of menthol analogs include WS-23, WS158 and other phosphine oxide menthol analogs, menthoxypropane-1,2-diol and cyclic alpha-keto enamines such as 4-methyl-3-(1-pyrrolidinyl)-2-[5H]-furanone.

Examples of local anesthetics include dibucaine hydrochloride, dibucaine, lidocaine hydrochloride, lidocaine, benzocaine, pramoxine hydrochloride, tetracaine, tetracaine hydrochloride, oxyprocaine hydrochloride, mepivacaine, piperocaine hydrochloride, etc.

Examples of antibiotics include neomycin the anti-viral agent docasanol (Abreva®), and examples of keratolytics include such agents as, alpha-hydroxy acids, glycolic acid and salicylic acid.

In practicing the present invention, the topical administration of icilin relieves itching, especially when given in combination with a menthol analog. A suitable menthol analog is, for example WS-158, a phosphine oxide menthol analog synthesized by Wilkinson Sword Company [Watson, H. R., R. Hems, D. G. Roswell & D. J. Spring, New compounds with the menthol cooling effect, J. Society Cosmetic Chemists. 29, 185–200 (1978)]. The duration of the cold effect for this combination lasts for more than 4 hours whereas normal menthol analogs alone seldom act longer than 1 hour. Thus a particularly preferred embodiment is formulated as a liniment (e.g. a lotion, cream or ointment) for atopic dermatitis and includes icilin, a menthol analog, and an anti-inflammatory glucocorticosteroid. Such a medication is useful for human therapeutics as well as for veterinarian uses.

Examples of menthol analogs include WS-3 and WS-23, both menthol analogs having Generally Recognized As Safe status by regulatory authorities; WS-158 and other phosphine oxide menthol analogs; menthone glycerol ketal, menthyl lactate, menthoxypropane-1,2-diol and cyclic alpha-keto enamines such as 4-methyl-3-(1-pyrrolidinyl)-2-[5H]-furanone.

Treatment of Pain

A form of viral herpes disease is called herpes zoster, commonly known as shingles. Herpes zoster is a disease of middle or old age characterized by extreme pain in a limited area of the upper body or face and an outbreak of small pimply blisters in the same area usually along the nerve branches. The herpes zoster is caused by varicella-zoster virus, the same virus that causes chickenpox. Herpes zoster is an acute central nervous system infection involving primarily the dorsal root ganglia and characterized by vesicular eruption and neuralgic pain in the cutaneous areas supplied by peripheral sensory nerves arising in the affected root ganglia in which the inflammatory changes occur. There is no specific therapy for this extremely painful viral infection. Corticosteroids, if given early, may relieve pain in severe cases. Aspirin and other anti-inflammatories or antiviral agents systemically may alleviate the pain. Thus, it is possible that compositions including icilin would alleviate the pain connected with the symptomatically occurring blisters during a herpes zoster attack.

Some of the most difficult orofacial pain problems faced by clinicians and dentists are those without an obvious pulpal, periodontal or mucosal cause. This important group of "pains" is given the title of idiopathic facial pain. One variant of orofacial pain, called atypical odontalgia, is one in which facial pain is diagnosed in the absence of detectable pulp or periodontal pathology. This condition presents as a severe throbbing pain in a tooth or teeth simulating pulpitis, periodontitis or unusually sensitive dentine (dentinal allodynia). Other intraoral symptoms are collectively described as oral dysesthesia and include a burning discomfort in the tongue (glossopyrosis) and gingiva or lips, a persistently "dry mouth" in the presence of saliva, or conversely the complaint of excessive saliva both without any detectable abnormality. Another feature is a disturbance of taste, often described as being metallic or purulent, and the patient may insist on suffering a persistent infection of the teeth or nasopharynx and halitosis. I believe it likely that icilin lozenges may relieve some of the symptoms of this atypical pain condition.

Menthol, being a small lipid-soluble molecule, immediately diffuses to its sites of action, namely, sensory nerve endings in the mucous membranes of the mouth and throat. Such are the effects of mentholated candy and chewing gum. By contrast, the actions of the less soluble icilin are modulated by the mode of drug delivery. Thus, if mixed as a solid with saliva in chewing gum, the primary sites of icilin action would be on nerve endings in the esophagus and stomach, as it passes into the upper alimentary tract. If an action of icilin on the mucous membranes of the mouth is desired, the drug may be formulated into a more soluble form and administered as a lozenge. Such a formulation, for example, in propylene glycol or as powder form in other appropriate vehicles, would permit a more localized action of icilin in the buccal cavity.

Topical Delivery to Targets

Pharmaceutical carriers or vehicles suitable for the topical administration of icilin and combinations provided herein include any such carriers known to those skilled in the art to be suitable for the particular mode of administration. In addition, the compounds may be formulated as the sole pharmaceutically active ingredient in the composition or may be combined with other active ingredients. The effective concentration may be determined empirically by testing the compounds using in vitro and in vivo systems. Thus, preferred carriers are dermatologically acceptable vehicles well known to the art. The cold receptor agonist of this invention may be dispersed in such a vehicle as an emulsion where it is either in solid form or is solubilized and is in either the aqueous or the oil phase.

The rate of drug absorption across the skin surface is dependent on drug concentration in the formulation, its water solubility and its oil/water partition co-efficient between the stratum corneum and the formulation. The physical form of icilin to be delivered to dermal receptors is optimized by design for penetration and sufficient duration of action. Although icilin may be administered dissolved in a solvent such as 1,2-propanediol, more preferably it is suspended as a solid in a liniment (emulsion) such as an ointment or cream, or it is administered as a dry powder admixed with other solids. In the solid form, icilin may be modified by re-crystallization to a particle with maximal surface area, or it may be incorporated onto nanospheres or incorporated into nanoparticles or liposomes, as such methods are now known in the art. For icilin to reach its target in the dermis, is must cross the skin by intracellular (through cells) or intercellular (between cells) routes. Occlusive bandages that increase the degree of skin hydration and prolong the contact of the drug with the skin enhance skin absorption of drugs across an intact skin, and are contemplated for practicing this invention.

Enhancers of skin penetration may usefully be included in embodiments of the invention and include certain surfactants, a drug such as azone, alcohol, acetone, propylene glycol and polyethylene glycol of appropriate molecular weight. Suitable surfactants include a common type of anionic synthetic surfactant are the sodium or potassium alkyl benzene sulfonates, in which the alkyl group contains from about 9 to about 15 carbon atoms. Non-ionic surfactants that may enhance retention on the skin and facilitate absorption are polyoxyethylene polymers. Representative of such agents are the esters or partial esters of fatty acids containing from 6 to 22 carbon atoms, such as octanoic, palmitic, stearic, linoleic, and oleic acids with an aliphatic polyhydric alcohol or its cyclic anhydride such as, for example, ethylene glycol, glycerol, erythritol, arabitol, mannitol, sorbitol, and the polyoxyethylene and polyoxypropylene derivatives of these esters.

It is well understood in the art that the precise dosage and duration of treatment is a function of the tissue being treated and may be determined empirically using known testing protocols or by extrapolation from in vivo or in vitro test data. It is to be noted that concentrations and dosage values may also vary with the age of the individual treated. It is to be further understood that for any particular subject, specific dosage regimens should be adjusted over time according to the individual need and the professional judgment of the person administering or supervising the administration of the formulations, and that the concentration ranges set forth herein are exemplary only and are not intended to limit the scope or practice of the claimed formulations.

The Formula 1 compounds are typically included at concentrations of 0.1% w/w up to 50% w/w or higher. Preferable concentrations are in the range of 0.5% w/w to about 25% w/w, more preferably 1% w/w to 25% w/w, yet more preferably greater than about 1% w/w to about 10% w/w, and most preferably greater than 1% w/w up to about 5% w/w. Aqueous suspensions and formulations contain 1% w/w or more.

Broadly, then, the suitable therapeutic compositions may be formulated as a solution, suspension, emulsion or the like, and may also be formulated as creams, gels, ointments, emulsions, solutions, elixirs, lotions, suspensions, tinctures, pastes, foams, aerosols, irrigations, sprays, suppositories, bandages, or any other formulations suitable for topical administration.

The composition of the present invention may be incorporated into an occlusive bandage containing at least one water-insoluble, pharmacologically approved, alkyl cellulose or hydroxyalkyl cellulose. Alkyl cellulose or hydroxyalkyl cellulose polymers for use in this invention include methyl cellulose, ethyl cellulose, propyl cellulose, butyl cellulose, cellulose acetate, hydroxymethyl cellulose, hydroxyethyl cellulose, hydroxypropyl cellulose, hydroxybutyl cellulose, and ethylhydroxyethyl cellulose, alone or in combination. For ethyl cellulose polymers, the preferred characteristics include an ethoxyl content between 42 and 52%, and more preferably between 44 and 50%, and for a 5% by weight of polymer in a 80/20 toluene/ethanol solution, a viscosity of between 2 and 500 cps, and more preferably between 4 and 400 cps. In addition, a plasticizer or a cross linking agent may be used to modify the polymer's characteristics. For example, esters such as dibutyl or diethyl phthalate, amides such as diethyldiphenyl urea, vegetable oils, fatty acids and alcohols such as acid oleic and myristyl may be used in combination with the cellulose derivative.

The solvent used for dissolving icilin may be a nonaqueous pharmacologically approved solvent with good penetration characteristics. Suitable organic materials useful as the solvent or a part of a solvent system are as follows: propylene glycol polyethylene glycol M.W. 200–600), polypropylene glycol (M.W. 425–2025), glycerine, sorbitol esters, 1,2,6-hexanetriol ethanol, isopropanol, diethyl tartrate, butanediol and mixtures thereof. Such solvent systems can also contain water. Some examples include ethoxydiglycol, and 1 methyl-2 pyrrolidone, and propanediols, alone or in combination. The preferred solvent for use in this invention is a propanediol containing 0.2 to 5% of icilin by weight.

For one example, an ointment containing icilin, 0.02 to 5% by weight, may be composed of emulsifying wax, white petrolatum and propylene glycol, butylated hydroxyanisole, propyl gallate, citric acid and lactic acid. A lotion containing icilin, 0.1 to 5% by weight, may be composed of a smooth, homogeneous, opaque emulsion composed of benzyl alcohol 2% (wt/wt) as preservative, emulsifying wax, glycerin, isopropyl palmitate, lactic acid, purified water, and polyethylene glycol 400.

For another example, an antipruritic ointment may contain the following ingredients: a homogeneous melt of 50.0% methyl salicylate, 25.0% white beeswax, 25.0% anhydrous lanolin to which is added 2% by weight of icilin and 1% by weight of 0.5% of di-sec-butyl-n-octyl phosphine oxide. The mixture is warmed and then allowed to solidify. A soft ointment results having a soothing effect on the skin accompanied by a cooling effect.

Solutions and suspensions for topical administration are formulated to contain an amount of one or more compounds effective to deliver an anti-pruritic amount, typically at a concentration of between about 0.1–50% w/w, preferably at least more than 1% w/w, more preferably more than 2% w/w of one or more of the compounds provided herein. The balance is water, a suitable organic solvent or other suitable solvent or buffer.

Solutions or suspensions used for local application can include any of the following components: a sterile diluent, such as purified water, saline solution, polyethylene glycol glycerine, propylene glycol or other synthetic solvent; antimicrobial agents, such as benzyl alcohol and methyl parabens; antioxidants, such as ascorbic acid and sodium bisulfite; chelating agents, such as ethylenediaminetetraacetic acid (EDTA); buffers, such as acetates, citrates and phosphates; and agents for the adjustment of tonicity such as sodium chloride or dextrose.

Liquid preparations can be enclosed in ampoules, disposable syringes or multiple dose vials made of glass, plastic or other suitable material Suitable carriers may include physiological saline or phosphate buffered saline (PBS), and the suspensions and solutions may contain thickening and solubilizing agents, such as glucose, polyethylene glycol, and polypropylene glycol and mixtures thereof. Suitably prepared solutions and suspension may also be topically applied to the eyes and mucosa. Solutions, particularly those intended for ophthalmic use, maybe formulated as 0.01%–10% w/w isotonic solutions, pH about 5–7, with appropriate salts, and preferably containing one or more of the compounds herein at a concentration of about 0.1% w/w preferably greater than 1% w/w, up to 50% w/w or more. Suitable ophthalmic solutions are known (see, e.g. U.S. Pat. No. 5,116,868, which describes typical compositions of ophthalmic irrigation solutions and solutions for topical application). Such solutions, which have a pH adjusted to about 7.4, contain, for example, 90–100 mM sodium chloride, 4–6 mM dibasic potassium phosphate, 4–6 AM dibasic sodium phosphate, 8–12 mM sodium citrate, 0.5–1.5 mM magnesium chloride, 1.5–2.5 mM calcium chloride, 15–25 MM sodium acetate, 10–20 mM D.L.-sodium .beta.-hydroxy butyrate and 5–5.5 mM glucose.

Treatment of Nasal Irritation, Stuffiness, and Congestion

The nose is the entrance to the respiratory tract. It serves as a conduit for inspired and expired air. When one or both sides of the nose are obstructed, this impairs nasal functioning and is perceived as an uncomfortable condition. All the nasal cavity bony surfaces, including the paranasal sinuses, are lined by tissue called mucosa. This mucosa contains blood vessels, nerves, and small glands that secrete fluids into the nasal cavity. The nose is also supplied by nerves (from the trigeminal branch) capable of detecting pain, temperature and pressure. The nasal mucosa functions to humidify and warm the inspired hair, hence it receives a large blood flow and the cells maintain a high degree of metabolic activity. Inflammation of the nasal mucosa caused by allergy, irritants or infections will cause the mucosa to swell. When the mucosa swells, the area available through which air can pass is diminished, and therefore one experiences a sense of nasal obstruction. The nose can also become "runny" (rhinitis) and the fluid discharge adds to the feeling of congestion. If either or both sides of the nose are obstructed, the asymmetry in airflow is perceived as an unpleasant condition.

As described below, icilin administered into the nasal cavity produces a sensation of increased airflow, refreshment and coolness, without any odor or sense of irritation.

The mechanism of this effect may be because the nasal mucosa is lined with vanilloid (capsaicin receptor 1, VR1) and cold receptors. The vanilloid receptor is linked to sensory nerve afferents that are activated by painful stimuli. Stimulation of these nerve fibers also lead to antidromic release of vasodilatory substances and inflammatory mediators such as histamine, substance P and calcitonin-gene related peptides, a process called neurogenic inflammation. Babes et al. [Cooling inhibits capsaicin-induced currents in cultured rat dorsal root ganglion neurones. Neurosci Lett 317: 131–134, 2002] have shown that reducing the temperature in dorsal root ganglion neurones inhibited discharge of the vanilloid receptor. The soothing and decongestant actions of icilin may be explained by such results. Icilin may mimic the cold inhibition of vanilloid receptor activity and hence reduce the inflammation occurring in the upper airways. It is known that neurogenic inflammation contributes to and exacerbates the signs and symptoms of asthma and other inflammatory disorders of the lungs [Barnes P J. Neurogenic inflammation in the airways. Respiratory Physiol 125: 145–154, 2001]. Hence reduction of neurogenic inflammation by icilin may also be beneficial in this condition as well as in allergic rhinitis, bronchitis, and chronic obstructive pulmonary disease. Stimulation of the vanilloid receptor (also called the capsaicin receptor after the active principle of chili pepper) can also evoke the cough reflex. Hence, the antitussive effects of icilin may be explained by this pathway. These sensory afferents also contribute to pharyngeal and throat reflexes that cause sleep apnea. Use of icilin for this condition may be warranted.

Delivery to Intranasal Cold Receptors

For delivery to the nose the pharmaceutical compositions of this invention may be administered by nasal aerosol to deliver the active ingredient onto mucosal surfaces for topical actions. Such compositions are prepared according to techniques well-known in the art of pharmaceutical formulation and may be prepared as solutions in saline, employing benzyl alcohol, benzalkonium chloride or other suitable preservatives, absorption promoters to enhance bioavailability and bioadhesiveness for prolonged contact, and/or other solubilizing or dispersing agents known in the art. Thus, a composition for administration to the intranasal or intrabuccal surfaces is particularly contemplated that comprises a solution of icilin dissolved or dispersed in a pharmaceutically acceptable diluent (carrier). The solvent may be 1,2-propanediol, 1,3-propanediol and a variety of aqueous carriers can be used, e.g. buffered water, 0.9 percent saline, buffered aqueous-ethanol solutions and the like. These compositions can be sterilized by conventional, well-known sterilization techniques, or can be sterile filtered. The resulting solutions can be packaged for use as is or mixed as an adjuvant to another medication. A composition can contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, etc.

An example of a nasal mist to which icilin may be added is Ayr® Saline Nasal Mist, which is an isotonic saline (sodium chloride) solution, buffered with sodium phosphate, and preserved with disodium EDTA and benzalkonium chloride. An example of a nasal spray decongestant is Afrin® Severe Congestion Nasal Spray with Menthol, a product of Schering-Plough, Inc. It is used: "For the temporary relief of nasal congestion due to a cold, hay fever or other upper respiratory allergies or associated with sinusitis. Shrinks swollen nasal membranes so you can breathe freely." The active ingredients is oxymetazoline hydrochloride (0.05%), a sympathomimetic amine vasoconstrictor decongestant, and the inactive ingredients are listed as benzalkonium chloride, benzyl alcohol, camphor, edetate disodium, eucalyptol, menthol, polysorbate 80, propylene glycol, sodium phosphate dibasic, sodium phosphate monobasic, and water. Similar items for upper respiratory ailments, including the common cold, cough and bronchitis, are products of Vicks Corporation, a division of Proctor and Gamble. These products include Vapor Inhaler® (levamphetamine, as a nasal decongestant), VapoRub® containing menthol and camphor, and VapoSteam® containing camphor, a chemical similar to menthol. It is expected that icilin alone or as adjunct to like products can achieve an equal if not better treatment of nasal mucosal inflammation.

The concentration of icilin utilized is usually at or at least about 0.10 percent to as much as about 2 percent by weight and is selected primarily by fluid volumes, in accordance with the particular mode of administration selected. Thus, a typical pharmaceutical composition for delivery can be made up to contain about 0.25 mg/ml to about 150 mg/ml of the icilin. Actual methods for preparing compounds are known or apparent to those skilled in the art. For use in combination with menthol analogs, the ideal molar ratio of icilin to menthol analog is about 1 to 1, with a range of 1 to 0.5, 2 to 1, and 3 to 1.

A second form of delivery of icilin to the nasal cold receptors is to administer icilin in powder form; by itself or admixed to an inert carrier such as calcium carbonate or lactose; or in conjunction with a nasal condiment such as tobacco snuff. The icilin may be prepared in micronized form, by granulation, drying, and sizing or milling to a specified particle size and thus to have a high surface area for interaction with cold receptors. An excipient (inert substances that form a vehicle for the active ingredients) such as lactose may be used for formulation to obtain uniform consistency and a uniform drug loading.

Delivery to Bronchial Cold Receptors

The surface of the nasal cavities and the bronchi and bronchioles contain nerve endings that generate the sensations that initiate sneezing and cough. By producing a non-irritant, non-odorous stimulation of cold receptors, the desire to sneeze and cough is diminished. For aerosol administration to portions of the upper respiratory tract, a contemplated icilin is preferably supplied in solution such as aqueous propylene glycol solution along with surfactant and propellant. Typical percentages of a icilin or about 0.05 percent to about 2 percent by weight, and preferably about 0.05 percent to about 0.5 percent. The surfactant must of course, be nontoxic, and preferably soluble in the propellant. Representative of such agents are the esters or partial esters of fatty acids containing from 6 to 22 carbon atoms, such as octanoic, palmitic, stearic, linoleic, and oleic acids with an aliphatic polyhydric alcohol or its cyclic anhydride such as, for example, ethylene glycol, glycerol, erythritol, arabitol, mannitol, sorbitol, and the polyoxyethylene and polyoxypropylene derivatives of these esters. Mixed esters, such as mixed or natural glycerides can be employed. The surfactant can constitute about 0.1 to about 20 percent by weight of the composition, and preferably about 0.25 to about 5 percent. The balance of the composition is ordinarily propellant. Liquefied propellants are typically gases at ambient conditions, and are condensed under pressure. Among suitable liquefied propellants are the lower alkanes containing up to 5 carbons, such as butane and propane; or preferably fluorinated alkanes. In producing the aerosol, a container equipped with a suitable valve is filled with the appropriate propellant, containing the finely divided compounds and surfactant. The ingredients are thus maintained at an elevated pressure until released by action of the valve. A pump-activated spray using air as propellant (atomizer or nebulizer) is also contemplated. Another method for delivery of icilin is to prepare it by spray drying with a hydrophilic excipient, e.g. povidone, lactose, and deliver it using dry power inhalers. Such methods of drug preparations for inhalation have been described by Gordon et al. (U.S. Pat. No. 6,365,190). The advantage of this method for icilin is that it may have a more prolonged action when administered in dry power versus in soluble forms.

Treatment of Eyelids and Eye Surface

The irritants that generate itch and sneezing in the nasal cavity and cough in the upper airways also irritate the eye. The eyeball is a dynamic system of fluid secretion and sensory nerve endings. Minor irritation evokes blinking and lachrymation. It is known to this art that certain patients suffer from ocular and/or palpebral sensations of itching or pruritus and dysesthesic sensations around the eyes and eyelids. These pruritic or dysesthesic sensations may be of allergic origin, of infection, or of tissue injury. By the term "dysesthesic sensations" are intended sensations of burning or heating, stinging, tingling, strain, discomfort and tightness. These sensations may be combined with redness. Together, these conditions are also called "pink eye" or conjunctivitis. Among the factors triggering ophthalmic or palpebral pruritic or dysesthesic afflictions, exemplary thereof are rapid temperature variations, heat and in particular exposure to ultraviolet or infrared radiation, low relative humidity, exposure to violent winds or to currents of air (blowing machine, conditioned air), the application of surfactants, exposure to toxic or irritant vapors or to dusts, irritant topical products, irritant dermatological or cosmetic palpebral topical products or the use of certain cosmetics, even when these are not known to be particularly irritating. Other factors triggering ocular or palpebral prurigintic or dysesthesic afflictions which should also be included are allergens such as, in particular, pollen, animal hairs, acarians and molds. The pathological mechanism of these signs are poorly understood and ocular and/or palpebral dysesthesias are treated with corticoids and also local antiseptics as an ophthalmic ointment or as drops. Although corticoids are relatively effective at alleviating the above symptoms, they have side effects which are often severe, such as atrophies and super-infections.

Thus, prior art treatments of the aforesaid ocular and palpebral dysesthesias, pains and pruritus have significant drawbacks and disadvantages, which are overcome by practice of the present invention.

An icilin eye-drop preparation may consist of each milliliter of buffered ophthalmic solution in a suitable ophthalmic dispenser containing icilin, dissolved in an approved non-irritating solvent such as 1,2-propanediol, equivalent to 0.1 to 5 mg/ml (%) icilin, and inactive ingredients: creatinine, sodium citrate, sodium borate, polysorbate 80, disodium edetate, adjusted pH to 6.6–7.2, and water. Benzalkonium chloride 0.02% and sodium bisulfite 0.1% are added as preservatives. This solution may also contain adjunct drugs such aqueous soluble steroids (e.g. dexamethasone sodium phosphate) and antibiotics (e.g. neomycin). To prolong duration of action on the eyelids and eye surface, icilin may also be administered as a micronized particle suspended in solution, admixed with an inert carrier, or with an inert binding substance, e.g. alginate. An example of an opthalmic solution to which icilin may be added is Neodecadron®. Each milliliter of buffered Ophthalmic Solution NEODECADRON in the OCUMETER ophthalmic dispenser contains: dexamethasone sodium phosphate equivalent to 1 mg (0.1%) dexamethasone phosphate, and neomycin sulfate equivalent to 3.5 mg neomycin base. Inactive ingredients: creatinine, sodium citrate, sodium borate, polysorbate 80, disodium edetate, hydrochloric acid to adjust pH to 6.6–7.2, and water for injection. Benzalkonium chloride 0.02% and sodium bisulfite 0.1% are added as preservatives.

Other contemplated uses of icilin in therapy are to cope with a hostile environment in which temperature and irritants are elevated. For example, in the Vietnam war, soldiers in the field suffered from heat stroke because water at ambient temperatures was "too hot to drink." Attempts to improve the palatability of water with large amounts of flavoring (Kool-Aid) were marginally successful. In another military situation, war in the Persian Gulf requires protection of all skin surfaces against chemical agents with airtight suits at ambient temperatures of greater than 40° C. Body heat management can become intolerable under these situations. A cooling agent such as icilin administered in eyedrops, a nebulized mist, an inhaler, syrup, lozenge, chewing gum or capsule would allow an individual to cope with a hot and noxious environment. Similarly, firefighters during a fire may benefit from symptomatic relief from heat and smoke, and city-dwellers would find such an agent refreshing in conditions of excessive heat and pollution. Menthol because of its harsh taste at high concentrations, odor, flavor, and limited duration of action would not be as effective as icilin.

Treatment of Enteric Mucosa

The gut is a complex organ with many intrinsic components of the nervous system that function to regulate motility, sensations, digestion and secretion. It is known that the gut mucosa contains sensory afferents (A delta and C) fibers that code for thermal and nociceptive signals. Disruption of the enteric nervous system is thought to contribute to disorders such as the irritable bowel syndrome in which there is abdominal pain, a sense of distension, decreased or increased frequency of bowel movements and flatulence. It has been shown that enteric-coated capsules containing peppermint oil have beneficial effects on patients with the irritable bowel syndrome. Peppermint oil is 30 to 55% menthol and it is thought that menthol is the active ingredient. In double-blind placebo-controlled studies, the frequency of abdominal pain, discomfort of abdominal distension, bowel movements, borborygmi and flatulence were decreased by encapsulated peppermint oil (Colpermin®). It was hypothesized that the menthol content of peppermint oil may locally diminish the afferent discharge of sensory nerve endings to evoke irritability in the enteric mucosa.

Peppermint oil has been used for treatment of the irritable bowel syndrome but there are uncertainties about the toxic properties of this oil in humans. Peppermint oil is a complex mixture of substances and it contains pulegone, a recognized hepatotoxin [Nair, B., Final report on the safety assessment of Mentha Piperita (Peppermint) Oil, Mentha Piperita (Peppermint) Leaf Extract, Mentha Piperita (Peppermint) Leaf, and Mentha Piperita (Peppermint) Leaf Water. Int. J. Toxicol. 20 Suppl 3: 61–73; 2001]. Formulations of pure chemicals such as icilin and/or menthol analogs have not yet been used for the treatment of disorders of the lower alimentary tract. The formulation of icilin-resin complexes that avoid upper gastrointestinal absorption would allow localized delivery of icilin to the colon and thus attenuate the nervous irritability of this tissue. Ideally, an enteric-coated capsule including icilin, designed to withstand the acidity and digestive juices of the stomach and the small intestine, may be used alone or in combination with menthol or a menthol analog to treat irritable bowel disease. General formulations for water-insoluble drugs for colonic delivery of drugs have been described.

In one preferred embodiment, icilin in an enteric coating is administered via oral ingestion. The effective amount of icilin can be locally administered to the colon of the patient by oral ingestion of a unit dosage form such as a pill, tablet or capsule, comprising an effective amount of icilin which is enterically coated so as to be released from the unit dosage form in the lower intestinal tract, e.g., in the distal ileum and in the colon of the patient. A preferred unit dose is wherein icilin is present in an amount of about 10 mg to about 30 mg per pill, tablet or capsule. Enteric coatings remain intact in the stomach, but will dissolve and release the contents of the dosage form once it reaches the region where the pH is optimal for dissolution of the coating used. The purpose of an enteric coating is to substantially delay the release of the icilin until it reaches its target site of action in the ileum or colon. Aqueous film-coating technology is employed for the enteric coating of pharmaceutical dosage forms. Delayed-released oral icilin dosage forms have the potential advantage of delivering nearly all the icilin to the ileum or colon in an easily administered form.

Thus, a useful enteric coating is one that remains intact in the low pH environment of the stomach, but readily dissolved when the optimum dissolution pH of the particular coating is reached. This can vary between pH 3 to 7.5 depending upon the chemical composition of the enteric coating, but is preferably between about pH 6.8 and pH 7.2. The thickness of the coating will depend upon the solubility characteristics of the coating material and the site to be treated. The most extensively used polymer for enteric coating is cellulose acetate phthalate (CAP). However, CAP has an optimum dissolution pH greater than 6, thus early drug release may occur. Another useful polymer is polyvinyl acetate phthalate (PVAP), which is less permeable to moisture and gastric fluid, more stable to hydrolysis and able to dissolve at a lower pH, which could also result in early release of icilin in the duodenum. Another available polymer is hydroxypropyl methylcellulose phthalate. This has similar stability to PVAP and dissociates in the same pH range. Further examples of currently used polymers are those based on methacrylic acid, e.g., methacrylic acid ester copolymers with acidic ionizable groups. Dosage forms coated with methacrylic acid polymers dissolve in the ileum at about pH 6.8, and in the terminal ileum and caecum at about pH 7.2. In general coating thicknesses of about 25 to 200 microns, and especially 75 to 150 microns, are preferred using about 3 to 25 mg, preferably 8 to 15 mg of acidic coating material per square centimer of tablet or capsule surface. The precise coating thickness will however depend upon the solubility characteristics of the material used and the site to be treated. Suitable technologies for encapsulation and drug delivery are described by Sandborn et al. (U.S. Pat. No. 6,166,044), incorporated by reference.

In summary, I believe that no investigations of icilin in humans have been reported in the scientific literature other than what is discussed or described here. I point out the unique properties of icilin, note its differences from menthol, and describe novel compositions and preferred embodiments for therapeutic methods of use.

In the below experimental section, Example A describes a preparation of icilin and analogs, while Examples 1–7 describe therapeutic uses of the invention with human subjects.

Experimental

EXAMPLE A

Chemical Synthesis of Icilin and Analogs. The methods of chemical synthesis are as described by Podesva and Do Nascimento U.S. Pat. No. 3,821,221. Briefly, a substituted acetophenone, e.g. 3-nitroacetophenone or 3-trifluoromethylacetophenone, readily obtainable from commercial sources such as Sigma-Aldrich, Co., is mixed with diethylamine or dimethylamine in formaldehyde and refluxed in acidic solutions. After addition of a second substituent, the Mannich reaction produces a β-amino-ketone compound which is isolated. This reagent is then reacted with potassium cyanate or sodium cyanate to produce an unstable urea intermediate that proceeds to cyclize into the tetrahydropyridimine-2-one ring, with the appropriate groups on position 1 and 4 of the 1,2,3,6-tetrahydropyrimidine-2-one ring. The precipitated product is readily collected by filtration and may be recrystallized using solvents such ethyl acetate or purified on silica gel columns. The final products are solids stable at room temperature.

EXAMPLE 1

A female subject with hay fever and atopic dermatitis put on a wool turtle-neck sweater for 10 minutes. Itching and a pink colored rash developed within 30 to 45 minutes on the surface of the neck. A quarter of a milliliter of a 1,2-propanediol solution containing 20 mg/ml icilin and 20 mg/ml of WS-3, a menthol analog, was applied to the neck areas that were red and pruritic. Cooling sensations were felt at the site of drug application and the desire to scratch was diminished. These effects lasted for about 1.5 hours.

EXAMPLE 2

A male subject with inflamed hemorrhoids self-administered a commercial suppository, shaped as a 1.5-inch bullet, containing 25 mg of hydrocortisone. The suppository was coated with 5 mg of icilin and 5 mg of WS-23, a menthol analog. Cooling sensations were felt within 5 minutes in the anorectal area extending to the scrotum. Relief of discomfort and itch in the anorectal area lasted for longer than 3 hours. In a similar experiment, icilin, dissolved 20 mg/ml in propylene glycol was admixed with a isotonic sodium chloride solution laxative (containing monobasic sodium phosphate and dibasic sodium phosphate salts), and 2 ml of the emulsion was instilled into the rectum. Again, cooling sensations with relief of itch and discomfort were obtained for 2 hours.

EXAMPLE 3

A male subject with an abrasion on his finger (caused by friction) of about 1 square centimeter received 0.8 mg of icilin applied directly to the wound with a swab stick. The dull pain previously present at the wound site began to feel cold and the pain was lessened. The sensation of cold at the wound site was not prolonged and did not spread to a larger sensory field. These results show that icilin can penetrate abraded or inflamed skin to achieve an antinociceptive action, similar to the effect obtained by applying ice to injured tissues. Crystalline menthol applied to the same site did not elicit sensations of coldness or pain reduction.

EXAMPLE 4

A small quantity of a 10 mg/ml solution of icilin dissolved in propylene glycol was applied with a cotton swab stick to the lower eyelid of a male subject. Prickling sensations of cold were experienced on the lower eyelid within 10 minutes and the eyelids felt refreshed. This effect lasted for about 45 minutes. Crystals of menthol brought to the lower eyelid of this same subject initially elicited a sense of sharp discomfort. The eyelids smarted from the harsh irritant actions of menthol. The individual blinked and the eyes were momentarily closed with a small degree of lachrymation. But, after about 1 minute, this discomfort dissipated and the cooling sensations of menthol were felt on the eyelid. The sensations were refreshing and lasted for about 15 minutes and accompanied by a minty odor.

These results show that icilin can be applied to the mucous membranes of the eyelid without acute irritation and that sensations of coolness are readily obtained. By contrast, menthol cannot be used in eye drops because of its irritant actions.

EXAMPLE 5

A male subject, suffering from hay fever (in this case, seasonal allergy to grass pollen) stopped taking antihistamines for 24 hours and inhaled via the nose 0.5 mg or 2 mg (on 2 separate occasions) of icilin in powder form. No odor was detected. After drug administration, a sense of free and unobstructed airflow in the nasal cavity was experienced for about 3 hours. In the outdoors on a hill at an ambient temperature of 18° C., the sensation of breathing after icilin was that of inhaling a refreshing sea breeze. The presence of nasal discharge (allergic rhinitis), the urge to sneeze (pruritus) and the presence of itchy eyelids were curtailed and terminated by the icilin; but returned when the cold sensations diminished after 3 hours. A similar result was derived by inhalation of 0.8 mg of the acetoxy, fluoro and trimethylfluoro form of icilin but the degree of coldness and duration of action was less than that of icilin. Under identical circumstances, the inhalation of menthol crystals also produced a cooling and refreshing sensation but was accompanied by a mint flavor and an initial burning sensation. The duration of the menthol cooling effect that was achieved with 0.8 mg of menthol was 25 to 30 minutes. No overt beneficial effects were observed on the degree of nasal discharge or the urge to sneeze. Also, the eyes watered from the stinging sensations of menthol.

From these experiments, it is concluded that icilin and its analogs have 1) a prolonged cooling and refreshing action on the nasal surfaces that is not accompanied by odor or irritation, 2) a decongestant action on the nasal mucosa and 3) an anti-pruritic effect.

EXAMPLE 6

Icilin, dissolved in propylene glycol, was added to a commercial preparation of an anti-allergy nasal spray containing fluticasone to attain a concentration of about 10 mg icilin/ml solution. When sprayed into the nasal cavity the sensory qualities of icilin, as described in Example 5, were obtained. Thus, the presence of the anti-inflammatory glucocorticoid did not interfere with the actions of icilin. These results indicate that icilin can be used as an adjunct in anti-inflammatory steroidal preparations.

EXAMPLE 7

Two mg of icilin was spread between two wafers of a fruit-flavored chewing gum and chewed for 5 minutes by a male subject. No sensations of coolness were noted in the mouth or throat. But after 12 minutes general sensations of coolness were felt in the thoracic internal structures behind the sternum, in the epigastric area. These cooling effects lasted for about 45 minutes. By contrast, the chewing of mentholated gum or mentholated candy, produced after an initial harsh taste, strong cooling of the mouth and throat that lasted only about 10 minutes.

This experiment illustrates important pharmacokinetic differences between icilin and menthol. The effects of mentholated gum are immediate and localized to the mouth and throat. By contrast, icilin delivered as a powder admixed with saliva does not act until it reaches the lower esophagus. Further protection of the icilin by standard encapsulation technology will allow it to reach the distal portions of the gastrointestinal tract such as the lower ileum and colon where it may exert its pharmacological effects as a cold receptor agonist.

It is to be understood that while the invention has been described above in conjunction with preferred specific embodiments, the description and examples are intended to illustrate and not limit the scope of the invention, which is defined by the scope of the appended claims.

It is claimed:

1. A method of treating pruritus in a mammalian patient comprising: topically administering a therapeutically effective amount of a cold receptor agonist to skin of the patient, the agonist having the formula 1-[R.1-phenyl]-4-[R2-phenyl]-2,3,6-tetrahydro-pyrimidine-2-one wherein R1 is hydroxy, chloro, fluoro, an alkyl of about 2 to about 4 carbon atoms, acetoxy, or trifluoromethyl and R2 is nitro, chloro, fluoro, an alkyl of about 2 to 4 carbon atoms or trifluoromethyl.

2. The method as in claim 1, wherein the cold receptor agonist is administered topically as a liniment.

3. The method as in claim 2, wherein the cold receptor agonist is administered in an ointment, lotion or emulsified form.

4. The method as in claim 1, wherein the cold receptor agonist administered further comprises an agent selected from the group consisting of an anti-inflammatory glucocorticosteroid, a local anesthetic, an anti-histamine, a local anesthetic, menthol or a menthol analog and mixtures thereof.

5. The method as in claim 1, wherein the cold receptor agonist is incorporated into an occlusive bandage.

* * * * *